(12) United States Patent
Kallmyer et al.

(10) Patent No.: US 7,913,015 B2
(45) Date of Patent: Mar. 22, 2011

(54) IMPLANTABLE MEDICAL DEVICE BUS SYSTEM AND METHOD

(75) Inventors: Todd A. Kallmyer, Tempe, AZ (US); Kevin K. Walsh, Peoria, AZ (US); Javaid Masoud, Shoreview, MN (US); Xander Evers, Arnhem (NL); John C. Stroebel, Blaine, MN (US); James Ericksen, North Oaks, MN (US); Mark A. Stockburger, Rush City, MN (US); Paul J. Huelskamp, Saint Paul, MN (US)

(73) Assignee: Medtronic, Inc., Minneapolis ( * ) Notice: Subject to any disclaimer, the term of this patent is extended or adjusted under 35 U.S.C. 154(b) by 167 days.

(21) Appl. No.: 12/366,946

(22) Filed: Feb. 6, 2009

(65) Prior Publication Data
US 2009/0204168 A1 Aug. 13, 2009

Related U.S. Application Data

(63) Continuation of application No. 11/192,474, filed on Jul. 29, 2005, now abandoned.

(51) Int. Cl.
*G06F 13/36* (2006.01)

(52) U.S. Cl. ........ 710/117; 710/110; 710/116; 710/125; 710/305

(58) Field of Classification Search .................. 710/110, 710/117, 124, 125, 116, 305; 623/3.1
See application file for complete search history.

(56) References Cited

U.S. PATENT DOCUMENTS

| | | | | |
|---|---|---|---|---|
| 4,205,373 A | * | 5/1980 | Shah et al. | 710/306 |
| 4,228,496 A | * | 10/1980 | Katzman et al. | 710/100 |
| 4,506,111 A | * | 3/1985 | Takenouchi et al. | 379/93.24 |
| 4,570,220 A | * | 2/1986 | Tetrick et al. | 710/306 |
| 4,586,128 A | * | 4/1986 | DeWoskin | 710/113 |
| 4,630,193 A | * | 12/1986 | Kris | 713/502 |
| 4,660,169 A | * | 4/1987 | Norgren et al. | 710/111 |
| 4,742,475 A | * | 5/1988 | Kaiser et al. | 700/278 |
| 4,791,629 A | * | 12/1988 | Burns et al. | 370/363 |
| 4,796,022 A | * | 1/1989 | Schenkel et al. | 340/825.52 |
| 4,818,985 A | * | 4/1989 | Ikeda | 710/107 |
| 4,853,847 A | * | 8/1989 | Ohuchi | 713/600 |
| 4,872,157 A | * | 10/1989 | Hemmady et al. | 370/400 |
| 5,083,260 A | * | 1/1992 | Tsuchiya | 710/113 |
| 5,132,967 A | * | 7/1992 | Kalajainen | 370/462 |
| 5,168,568 A | * | 12/1992 | Thayer et al. | 710/125 |
| 5,237,567 A | * | 8/1993 | Nay et al. | 370/438 |
| 5,297,144 A | * | 3/1994 | Gilbert et al. | 370/346 |
| 5,495,594 A | * | 2/1996 | MacKenna et al. | 710/11 |
| 5,608,881 A | * | 3/1997 | Masumura et al. | 710/310 |
| 5,701,421 A | * | 12/1997 | Miller et al. | 710/305 |
| 5,822,244 A | * | 10/1998 | Hansen et al. | 365/185.11 |
| 6,072,796 A | * | 6/2000 | Christensen et al. | 370/379 |

(Continued)

OTHER PUBLICATIONS

Zhen et al. IEEE Body Area Networks for Medical Applications. IEEE. 2007.*

(Continued)

*Primary Examiner* — Matthew D Spittle

(57) ABSTRACT

A bus system is provided for implantable medical devices. The bus system provides for flexible and reliable communication between subsystems in an implantable medical device. The bus system facilitates a wide variety of communications between various subsystems. These various subsystems can include one or more sensing devices, processors, data storage devices, patient alert devices, power management devices, signal processing and other devices implemented to perform a variety of different functions.

27 Claims, 7 Drawing Sheets

U.S. PATENT DOCUMENTS

| | | | | |
|---|---|---|---|---|
| 6,097,707 A * | 8/2000 | Hodzic et al. | | 370/321 |
| 6,411,302 B1 * | 6/2002 | Chiraz | | 345/545 |
| 6,414,971 B1 * | 7/2002 | James et al. | | 370/519 |
| 6,446,151 B1 * | 9/2002 | Fischer et al. | | 710/124 |
| 6,470,407 B1 * | 10/2002 | Losi | | 710/264 |
| 6,513,083 B1 * | 1/2003 | Fischer et al. | | 710/124 |
| 6,577,901 B2 * | 6/2003 | Thompson | | 607/60 |
| 6,589,187 B1 * | 7/2003 | Dirnberger et al. | | 600/508 |
| 6,654,845 B1 * | 11/2003 | Morris et al. | | 710/305 |
| 6,662,256 B1 * | 12/2003 | Foo | | 710/305 |
| 6,728,810 B1 * | 4/2004 | Ishibashi | | 710/124 |
| 6,813,514 B1 * | 11/2004 | Kroll et al. | | 600/509 |
| 6,823,140 B1 * | 11/2004 | Davidson | | 398/73 |
| 6,918,068 B2 * | 7/2005 | Vail et al. | | 714/56 |
| 6,980,850 B1 * | 12/2005 | Kroll et al. | | 600/509 |
| 6,993,379 B1 * | 1/2006 | Kroll et al. | | 600/510 |
| 7,058,740 B2 * | 6/2006 | Watanabe et al. | | 710/110 |
| 7,103,412 B1 * | 9/2006 | Kroll | | 607/17 |
| 7,166,076 B2 * | 1/2007 | Poliac et al. | | 600/490 |
| 7,172,555 B2 * | 2/2007 | Poliac et al. | | 600/490 |
| 7,214,192 B2 * | 5/2007 | Poliac et al. | | 600/490 |
| 2004/0125697 A1 * | 7/2004 | Fleming | | 367/19 |
| 2004/0153707 A1 * | 8/2004 | Ellerbrock et al. | | 714/4 |

OTHER PUBLICATIONS

Ortmanns et al. A 232-Channel Epiretinal Stimulator ASIC. IEEE Journal of Solid-State Circuits. vol. 42, No. 12. Dec. 2007.*

Oh et al. New Modulation Scheme for High Data Rate Implantable Medical Devices. IEEE. 2009.*

Kanukurthy et al. Data Acquisition Unit for an Implantable Multi-Channel Optical Glucose Sensor. IEEE. May 2007.*

* cited by examiner

IMPLANTABLE MEDICAL DEVICE BUS SYSTEM AND METHOD

RELATED APPLICATION

This application is a continuation of U.S. patent application Ser. No. 11/192,474, filed Jul. 29, 2005 entitled "IMPLANTABLE MEDICAL DEVICE BUS SYSTEM AND METHOD".

TECHNICAL FIELD

The present invention relates generally to implantable medical devices. More particularly, the present invention relates to bus systems in implantable medical devices.

BACKGROUND

Wide assortments of implantable medical devices are presently known and commercially available. These implantable medical devices include a variety of implantable cardiac devices. For example, implantable pulse generators (IPGs) are a type of cardiac device that is generally used to elevate the heart rate that is beating too slowly. This type of device is sometimes referred to as a Bradycardia device or a pacemaker. Another type of implantable cardiac device is an implantable cardioverter defibrillator (ICD). This type of device, often referred to as a Tachycardia device, generally provides burst pacing pulses or a defibrillation shock to the heart when the heart is beating too fast or goes into fibrillation. Another type of device is a cardiac resynchronization device that treats heart failure. Another type of device are monitoring devices that use one or more physiologic sensors.

Each of these types of implantable medical devices requires the use of several components to provide the desired functionality. For example, a typical implantable medical device includes one or more sensing devices (e.g., magnetic sensor, pressure sensor, motion sensor, ECG sensor), processors, data storage devices, patient alert devices, power management devices, signal processing and other devices implemented to perform a variety of different functions. The various subsystems require mechanisms to communicate between subsystems in the device. For example, a typical implantable medical device requires reliable communication between a variety of different sensing devices and a main processor. Other types of communication can include event and message communication.

Each of these different types of communication can have different requirements. Again, to use the example discussed above, communicating between sensing devices and the main processor can require periodic communication reliability delivered at precise time intervals to reduce jitter in the sensing data. In contrast, general message communication between subsystems typically does not require such precise timing delivery, but it can require the ability to send much larger messages.

Unfortunately, mechanisms for communicating between subsystems in implantable medical devices lack flexibility to effectively provide for different types of communication between subsystems without requiring a substantial redesign of the communication system and of the subsystems themselves. Thus, there remains a need for improved communication systems in medical devices that facilitate communication between subsystems, including the ability to deliver different types of data with different delivery requirements, while maintaining design and implementation flexibility.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The present invention provides a bus system and method for implantable medical devices. The bus system provides for flexible and reliable communication between subsystems in an implantable medical device, such as an implantable cardiac defibrillators, implantable pulse generators, and implantable cardiac monitors. The bus system is non-colliding and can be used to facilitate a wide variety of communications between various subsystems. These various subsystems can include one or more sensing devices (e.g., magnetic sensor, pressure sensor, motion sensor, ECG sensor), processors, data storage devices, patient alert devices, power management devices, signal processing and other devices implemented to perform a variety of different functions.

Figure 1:
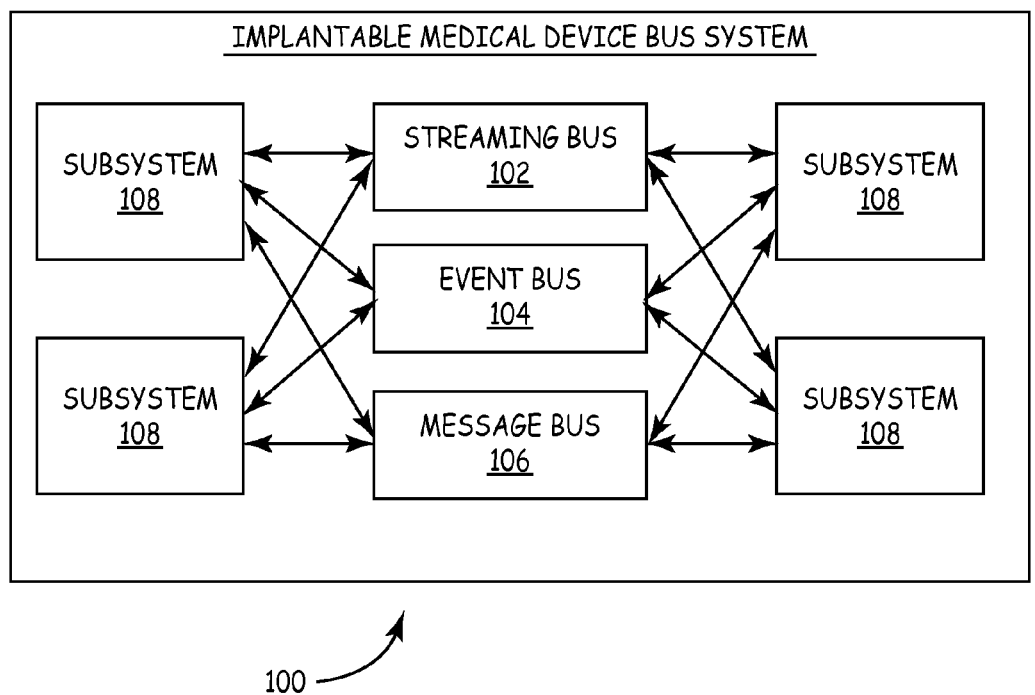
FIG. 1 is a schematic view of an exemplary implantable medical device bus system.

Turning now to FIG. 1, an exemplary implantable medical device bus system 100 is illustrated schematically. The bus system 100 includes a streaming bus 102, an event bus 104, and a message bus 106. Each of the different buses is implemented to provide a different type of communication between subsystems 108. In general, the streaming bus 102 is implemented to provide reliable, jitter-free communication of periodic sensing data between one or more sensing devices and other subsystems 108, such as the main processor. Conversely, the event bus 104 is implemented to reliably deliver event data that notifies subsystems 108 of important events in the implantable medical device. Finally, the message bus 106 is implemented to deliver relatively large messages between subsystems 108. It should be noted that in some implantable medical device applications, all three of these buses may not be implemented. For example, in some applications all bus functionality could be provided using the streaming bus for periodic sensor data and a message bus for both event data and general messages.

Figure 2:
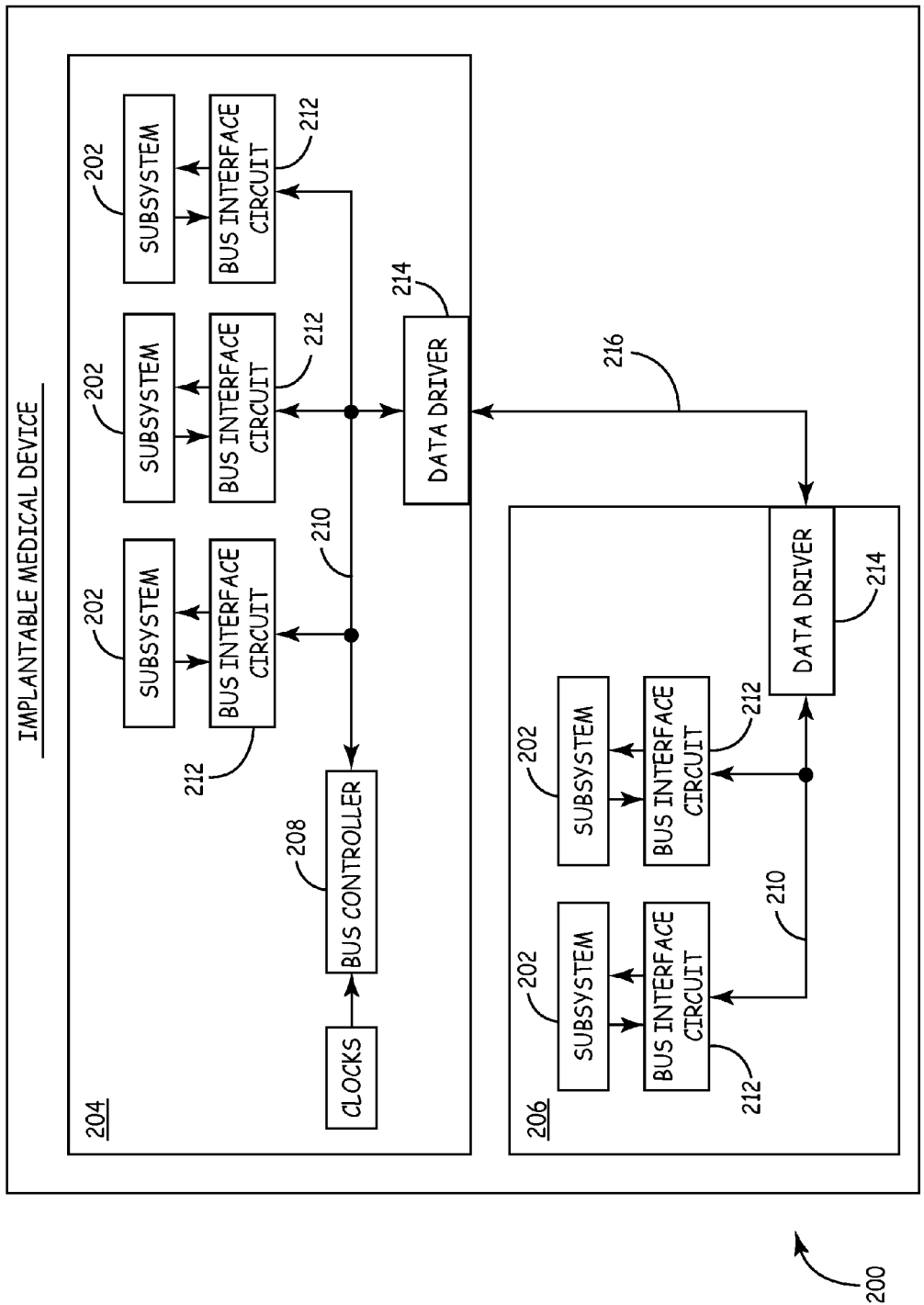
FIG. 2 is a simplified schematic view of an exemplary implantable medical device with a bus system.

Turning now to FIG. 2, an implantable medical device is 200 is illustrated schematically. The implantable medical device 200 includes five subsystems 202, three of the subsystems 202 residing on a first IC 204, and two other subsystems residing on a second IC 206. Again, the subsystems 202 can comprise any type of subsystem on an implantable medical device. Communication between the subsystems 202 is provided by the bus system. The bus system illustrated in FIG. 2 is meant to illustrate the common features of a streaming bus, event bus or message bus. The bus system includes a bus controller 208, bus conductors 210 and bus interface circuits 212. Additionally, in this embodiment, the bus system includes data drivers 214 and external bus conductors 216 for communicating between IC's.

In general, the bus controller 208 controls the bus system. For example, the bus controller 208 provides the clock signals used to control bus timing, arbitrates the allocation of time on the bus and generally controls the configuration of the bus. The bus conductors 210 are a plurality of conductive lines used to deliver data and control signals from the bus controller 208 to, from and between the bus interface circuits 212. As one example, the bus conductors comprises four separate data lines and two clock and control lines. The clock and controls lines are used to provide bus clocks and other signals between the controller 208 and the bus interface circuits 212. As will be described in greater detail below, these clocks can include bus clocks used to trigger data delivery and reconfiguration clocks to reconfigure the bus. The data lines deliver the streaming, event or message data between subsystems.

The bus interface circuits 212 provide the interface between the bus and the subsystems 202. Thus, the bus interface circuits 212 put data on, and retrieve data from, the bus as needed for their associated subsystem. The bus interface circuits 212 thus typically include data buffers and the mechanisms needed to transmit data to and from the bus. The bus interface circuits 212 would also include the mechanisms needed for communicating with their corresponding subsystem. The data drivers 214 and external bus conductors 216 provide for external communication between ICs. As such, the data drivers 214 convert the signals on the bus to an appropriate level for communication to and from an external IC.

Again, the bus system illustrated in FIG. 2 shows the common features of a streaming bus, event bus or message bus, each of which could be implemented separately on an implantable medical device. In an implementation of a streaming bus, the bus system provides for delivering periodic data between subsystems 202. The streaming bus is time sliced to provide precise timing and control for data on the bus. Specifically, the streaming bus assigns the subsystems 202 periodic time slices in which to transmit sensor data. Thus, the streaming bus provides the ability to deliver data at precisely controlled periodic time intervals. By delivering subsystem data at precisely controlled time intervals the streaming bus reduces the possibility of jitter in the data, improving the accuracy of the received data. This of particular importance when the data comprises sensor data from a sensor subsystem that must be delivered with little jitter and precise data rates. Additionally, by time slicing the bus and assigning different time slices to different subsystems, the streaming bus can precisely deliver sensor data from multiple different subsystems, all at their own precisely controlled periodic time interval. Thus, the streaming bus can be used to precisely deliver sensor data from a variety of different sensors, including ECG data, temperature data, acceleration data, blood volume data, or any of the other types of sensor data that can be used in an implantable medical device. This allows the streaming bus to be used in applications where precisely controlled bus latency is required. For example, the streaming bus can be used to send data within a pipelined analog-to-digital converter or digital signal processor.

Additionally, the streaming bus provides the ability to reconfigure the bus on the fly without disrupting the flow of data between the various subsystems 202. This allows additional subsystems 202 to be assigned time slices and/or for time slices to be reassigned to other subsystems 202 without interfering with delivery of other data on the bus. This reconfiguration can occur as a result of an event, such as activation of telemetry or a cardiac anomaly. For example, when a specified event is detected in one sensor, additional subsystems can become activated and need assigned time slices on the bus. In these cases the streaming bus is reconfigured by using a separate configuration clock and multiplexing configuration data on the bus between time slices. Thus, reconfiguration data can be provided to the various components on the bus, reassigning the time slices as needed to other components without interrupting the data on the time slices themselves. Thus, the streaming bus provides high flexibility of data transmission and while maintaining precisely controlled periodic data transmission.

In an event bus implementation, an event data bus is configured to send event data between subsystems 202, where the event data are fixed length, relatively short data messages. The event data are used to reliably indicate that an important event has occurred, and to pass data associated with the event. For example, event data can be sent to notify other subsystems that a cardiac event has been detected, which will in turn cause other systems to activate and respond. Because the event data are relatively short and of defined length each entire event data packet can be fully buffered at the transmitter and receiver. Specifically, the bus interface circuits for the event bus can be implemented with sufficient data storage to guarantee that event data can be received and buffered. This allows the transmitting subsystem to request an event data packet to be sent without requiring the transmitting subsystem to further monitor the bus. Full buffering allows transmitting and receiving subsystems to run at different clocks or in different states of activation. Thus, one subsystem can communicate with another subsystem, even while the other subsystem is inactive. This ability to communicate with other subsystems that are inactive facilitates a high level of fault tolerance in the system. Furthermore, because the messages are relatively short it can be assured that an event data will be sent relatively quickly, without having to wait for a very long message to complete. Thus, the event bus facilitates high reliability and high speed data transmission for the event bus messages.

In a message bus configuration, a message bus is configured to deliver different types of larger messages to and from the subsystems 202 in the implantable medical device. To best meet the different requirements of general message delivery, the message bus preferably includes the ability for data transfer synchronization of transmissions to multiple target subsystems 202. This ensures that messages need to be sent only once, thereby reducing the amount of power used to send messages to multiple target subsystems 202. In this technique, the bus controller 208 preferably sends a message header to all bus interface circuits 212 and waits for acknowledgement from each bus interface circuit 212 that they are ready to receive message data. When the message bus receives acknowledgement from each bus interface circuit 212 as to its readiness to receive the message, the message bus transmits the message to all of the subsystems at once. Thus, the message bus is able to reliably deliver the message while reducing the need for multiple transmissions that would otherwise waste significant power.

Figure 3:
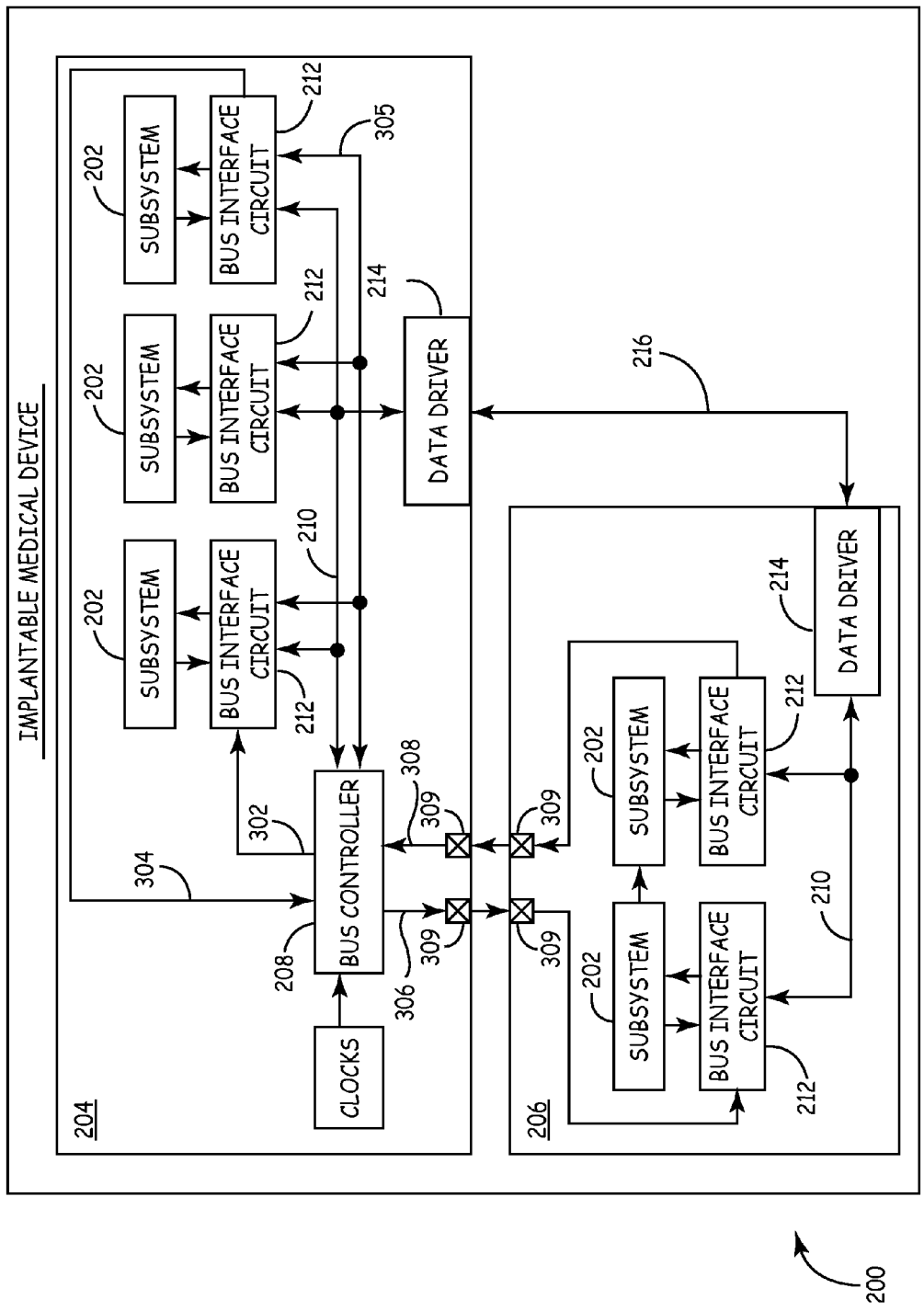
FIG. 3 is a simplified schematic view of an implantable medical device with a bus system.

It should be noted in an event bus and message bus implementation, the bus systems would also typically include priority lines and requests lines used by the bus interface circuits for the bus controller for arbitrating control of the bus. Turning now to FIG. 3, the implantable medical device bus system is illustrated with the addition of priority lines and request lines used to arbitrate control of the bus. The request lines are configured to link the subsystems and bus controller in a series chain. The priority lines connect the subsystems and bus controller in parallel. As will be explained in greater detail below, signals on the priority lines and the order in which the subsystems are linked by the request lines together determine the order precedence for arbitration on the bus.

Specifically, in the embodiment illustrated in FIG. 3, the bus system includes priority lines 305. The priority lines 305 are used by the bus interface circuits 212 to indicate that they have a priority message for the bus. Typically, the subsystems 202 would tell the bus interface circuits 212 when a message requires high priority. This could occur because the type of message is always prioritized, or because the message has been waiting too long for an opportunity to be put on the bus. In either the case, the bus interface circuit 212 indicates that it has a priority message by asserting a signal on priority lines 305. In one embodiment, the priority lines 305 comprise separate lines for internal messages and external messages. Thus, the bus interface circuit can indicate whether it has a priority message that is to be routed only the current IC, or if it has a priority message that needs to be routed to an external IC as well. These priority line signals are passed to the controller 208, which uses them to determine if the next data on the bus should be an internal message only, or one that is routed internally and externally. Typically, the bus controller 208 will route internally if only the internal priority line was asserted, and the bus controller 208 will route externally if only the external priority line was asserted. If neither or both lines are asserted, then the bus controller 208 will determine if the next message is to be routed externally based on other factors.

The request lines are identified by their relationship with the bus system controller. Thus, the bus system controller 208 is coupled to an OUT request line 302 and an IN request line 304, which are part of a series of request lines that connect bus interface circuits 212 in the first IC 204 in series. Likewise, the bus system controller 208 is coupled to an External OUT request line 308 and an External IN request line 306, which connect to the bus interface bus interface circuits 212 in the second IC 206. The external bus control lines are routed through request line drivers 309 that deliver and receive the request signal off the internal integrated circuit 204 to an external integrated circuit 206.

As illustrated in FIG. 3, the request lines are routed to create a chain of bus interface circuits 212 on the IC, with the bus controller 208 at the end of the chain. Thus, the request lines 302 and 304 are part of the chain of bus interface circuits 212 on the master IC 204, while request lines 306 and 308 are part of the chain of bus interface circuits 212 on the slave IC 206. The request lines are used by the bus interface circuits 212 to request control of the bus to send data, and are used collectively by the bus interface circuits 212 and controller 208 to arbitrate which bus interface circuit 212 is given control of the bus.

Specifically, each bus interface circuit 212 can request control of the bus by sending an appropriate signal down the chain from bus interface circuit 212 to bus interface circuit 212 until it reaches the bus controller 208. If the bus is not already on, the bus controller 208 will turn on the bus when a request is received.

Arbitration of the bus is determined by use of the priority lines, and also the order of the bus interface circuits 212 in the chain. In general, the bus interface circuits first determine if any of the other bus interface circuits 212 have requested priority. If only one bus interface circuit 212 has requested priority, then that bus interface circuit 212 is given control of the bus on the next bus clock cycle. If arbitration cannot be determined by the priority line alone, then the order of the bus interface circuits in the request line will be used to determine precedence. For example, if more than one bus interface circuit requests priority, or if no bus interface circuit requests priority, then the bus interface circuit 212 the farthest from the IN request line 304 to the bus controller is given precedence over other bus interface circuits 212. Thus, subsystem is hardwired by the order of subsystems as they are connected serially by the bus request lines, such as request lines 302 and 304 of FIG. 3. Thus, the bus system is arbitrated by determining if any bus interface circuit has requested priority first, and by the order of the bus interface circuits second.

Furthermore, the request lines will be used by the bus controller 208 to notify the bus interface circuit 212 when to stop data transmission and go to the next message. For example, when transmitting bus interface circuit 212 causes the request line to fall, the current message has stopped and the bus system can move to the next message. Thus, the falling request line tells the bus interface circuits 212 to again determine what bus interface circuit 212 gets to send the next set of data based on the priority lines and the order of the request lines.

Because of the use of the request line, message bus and event bus can be implemented to use very low amounts of power. Specifically, the bus systems can be implemented to turn off when not in use, conserving considerable power. Only when a request is sent from a bus interface circuit 212 on the request line will the other bus interface circuits 212 and bus controller 208 turn on. Thus, the bus clocks driven by the bus controller will only turn on when the bus is needed. Furthermore, the bus controller can hold the bus clock such that arbitration can be implemented to occur within a single bus clock.

The request lines can also be used to arbitrate a message based on whether the message is coming from a bus interface circuit 212 on an external IC or a bus interface circuit on the internal IC. Specifically, the chain of bus interface circuits 212 on the IC 204 can be coupled with the bus interface circuits 212 on the external IC 206 such that the external IC bus interface circuits 212 are given precedence over the bus interface circuits 212 on the internal IC 204. This can be accomplished by chaining the interface circuits 212 together in the bus controller 208 such that bus interface circuits 212 on the external IC get precedence.

Figure 4:
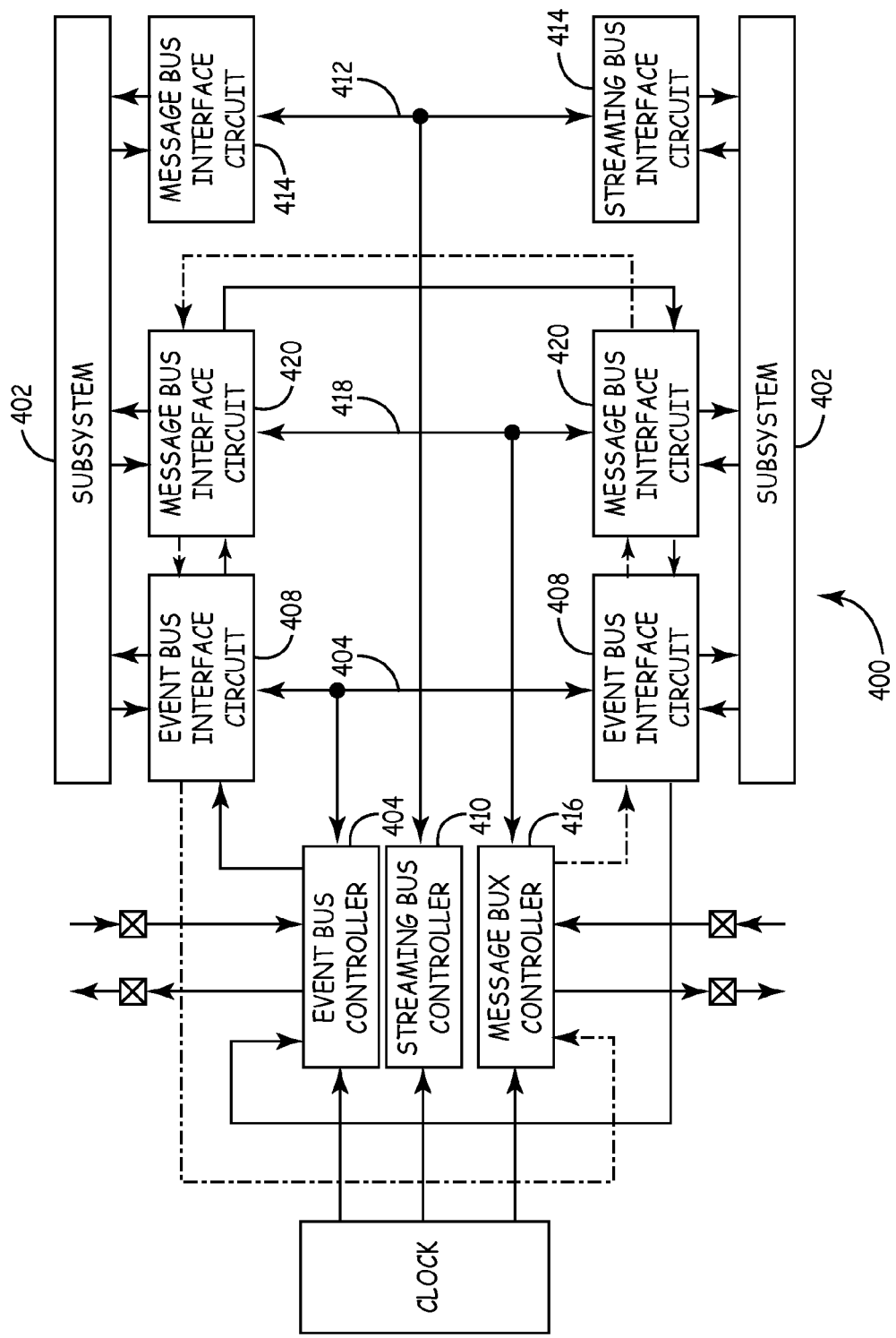
FIG. 4 a schematic view of an exemplary implantable medical device bus system.

Turning now to FIG. 4, a simplified example of three buses on an implantable medical device is illustrated schematically. In this simplified example there are two subsystems 402, with each of the subsystems coupled to an event bus, a message bus, and a streaming bus. The event bus includes an event bus controller 404, event bus conductors 406, and event bus interface circuits 408. The streaming bus includes a streaming bus controller 410, streaming bus conductors 412, and streaming bus interface circuits 414. The message bus includes a message bus controller 416, message bus conductors 418 and message bus interface circuits 420. The event and message bus also include request lines, including external request lines. Also, the event and message bus each include priority lines, which are not shown in this figure. Each of the bus controllers receives a system clock. From the system clock, the bus controllers generate all the other clocks that will be used for corresponding buses. Because all the clocks are generated from the system clock, the three buses can have a relatively high level of synchronization. For example, the frames in the streaming bus can be implemented to coincide with the event bus clock.

As stated above, the example illustrated in FIG. 4 is simplified. Typically, an implantable medical device would include more subsystems, with some of those subsystems residing on separate integrated circuits (ICs) and with external communication buses communicating between ICs as was illustrated in FIGS. 2 and 3. Each of the different buses is implemented to provide a different type of communication between subsystems 402. In general, the streaming bus is implemented to provide reliable, jitter-free communication of periodic sensing data between one or more sensing devices or other subsystems, such as the main processor. Conversely, the event bus is implemented to reliably deliver event data that notify subsystems of important events in the implantable medical device. Finally, the message bus is implemented to deliver relatively large messages between subsystems, including both read and write messages.

A detailed embodiment of an exemplary streaming bus system will now be described. As described above, the streaming bus is time sliced to provide precise timing and control for data on the bus. Specifically, the streaming bus assigns the subsystems periodic time slices in which to transmit sensor data and other types of data from the subsystems. Thus, the streaming bus provides the ability to deliver data at precisely controlled periodic time intervals. By delivering subsystem data at precisely controlled time intervals the streaming bus reduces the possibility of jitter in the data, improving the accuracy of the received data.

The streaming bus is preferably implemented as a plug-and-play digital interconnect. Streaming data would typically be sampled output bytes from sensors or analog-to-digital converters, but could also be low priority block transfers. The streaming bus is particularly applicable to applications where data transfer timing is constant, predictable and periodic once the bus is configured.

Conceptually, the streaming bus system is preferably layered, with each higher layer using the functions of the lower layers but not specifying their implementation. As one example, the streaming bus system can be conceptually layered into a system layer, application layer, session layer and a network layer. The system layer defines the overall functional objectives and partitions functions into different subsystems. The application layer is the subsystem user-level layer, served by the lower layers. The session layer manages data timing and buffering to the bus, configuration of source ID's, data recognition, and receiver buffering. The network layer controls bus routing, including the routing of data inside the master, internal IC and the routing to slave, external ICs.

The streaming bus provides a mechanism for subsystems to send periodic data bytes to each other with guaranteed timing. Each streaming data byte is broadcast in a specified time slice called a slot, with no destination address or label required to be added to the data. The streaming bus thus time-division multiplexes data from various sources onto the bus. The streaming bus is configured with a number of slots repeating in a unit called a frame. The assignment of slots to the various subsystems is programmed for efficiency. Furthermore, the assignment of slots can be reconfigured in such a way that synchronization and periodicity is maintained.

Figure 5:
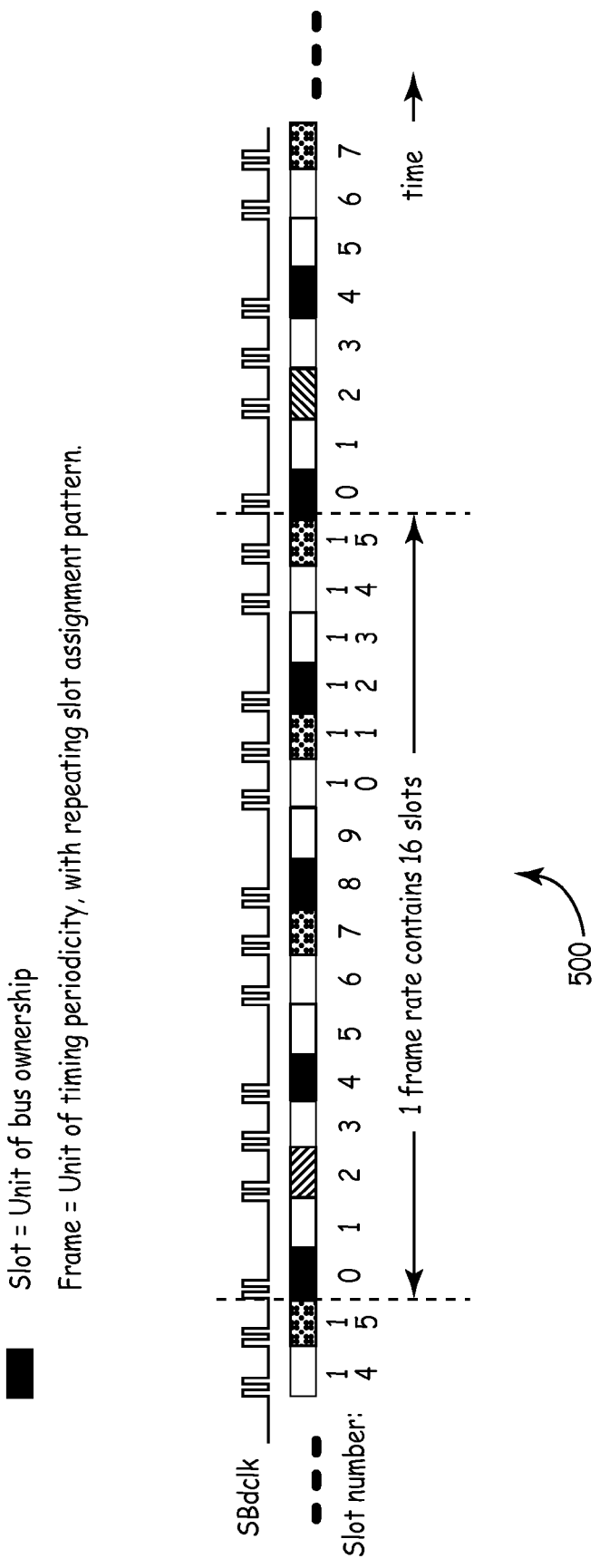
FIGS. 5-7 are exemplary timing diagrams for a streaming bus.

Turning now to FIG. 5, an exemplary timing diagram 500 illustrates how the streaming data bus can be time multiplexed. Specifically, FIG. 5 shows a timing diagram of a streaming bus data clock (SBdclk) and the associated data on the bus. In this example, the bus is multiplexed into 16 slots per frame. The controller sends a streaming bus data clock SBdclk signal for each of the slots that are used. Thus, those slots that are not proceeded by an SBdclk signal do not include data. This again saves power by reducing the of clock transitions.

Because each source of data transmits in an assigned slot, the bus interface circuits can identify bytes of streaming data by their slot position in the streaming data frame. Because of this, the streaming bus protocol can offer several advantages. For example, the bus can again provide high power efficiency, as only needed data is on the bus, without requiring other bits for addresses or labels.

By assigning each subsystem slots in the bus, access and timing are guaranteed for each subsystem. Furthermore, by assigning multiple slots per frame to the same subsystem, data transmitted on the bus can have different rates. For example, one subsystem can transmit in four slots per frame, while another subsystem transmits in only one slot per frame. Additionally, slower rates of transmission can be provided by assigning subsystems to alternating frames, or configuring subsystems to skip several frames between transmissions. Thus, the bus can accommodate the different transmission rate requirements of different subsystems.

In addition to the bus data clock SBdclk, the bus system preferably includes other clocks to synchronize and support reconfiguration. Specifically, it is desirable to include an event reference clock (ESclk) to synchronize the various subsystems on the different buses. The event reference clock is preferably synchronous with the frame rate used by the streaming bus. This guarantees that event data used to instruct the streaming bus controller on how to allocate the slots are fully transmitted before streaming bus reconfiguration will start at the next frame boundary. Additionally, the ESclk can be used by the subsystems to know that data from the buses is stable. To ensure that the data on the bus is stable the bus controller will not allow bus clock edges to coincide with ESclk. This can be done by pausing any other bus clocks (e.g., event bus clock EBclk, message bus clock MBclk, streaming bus data SBdclk, streaming bus configuration SBcclk) when they are near an ESclk edge.

Figure 6:
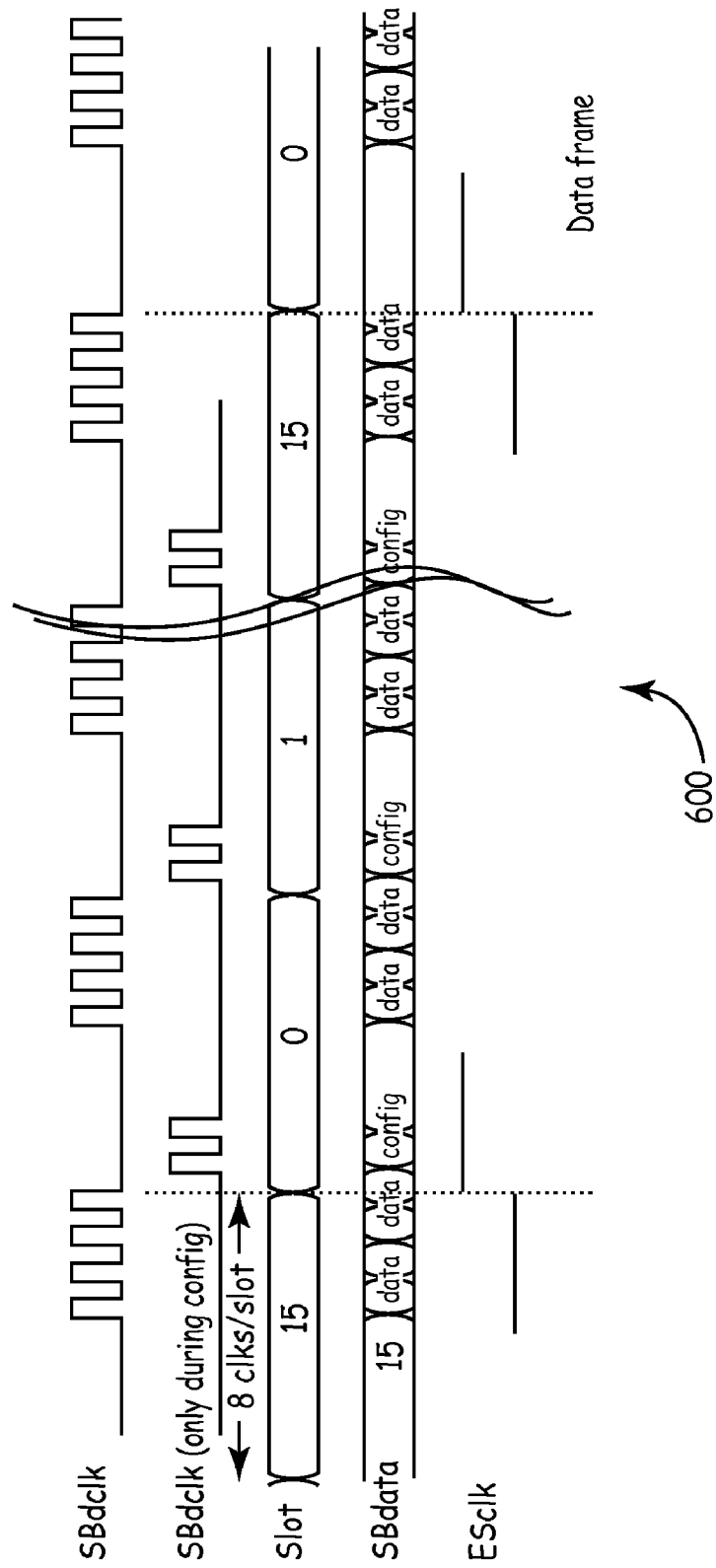

The data bus can have one or more data bits in parallel. For example, the data bus SBdata can be preferably four bits wide. Turning now to FIG. 6, a timing diagram 600 illustrates exemplary timing between a streaming bus data clock (SBdclk), streaming bus configuration clock (SBcclk), event reference clock (ESclk), and the slots and data on the streaming bus (SBdata). In this example, four data clocks and two configuration clocks fit into each slot, allowing each slot to carry 1 byte of configuration data (two sets of four bits on the four bus data lines) and 2 bytes of data (four sets of four bits on the four bus data lines). As described above, the data clock is used to indicate the presence of data in a slot on the bus. Thus, normal data transfer is synchronized by SBdclk. Again, the event reference clock ESclk is used to provide synchronization between events and frame boundaries. Finally, as will be described in greater detail below, the configuration clock is used to facilitate reconfiguration of the bus by reassigning associated slots. Typically, the SBcclk would only be used briefly during reconfiguration. Not shown in FIG. 6, asynchronous system reset of the streaming bus interface circuits and the bus controller are provided by SBreset signal.

Figure 7:
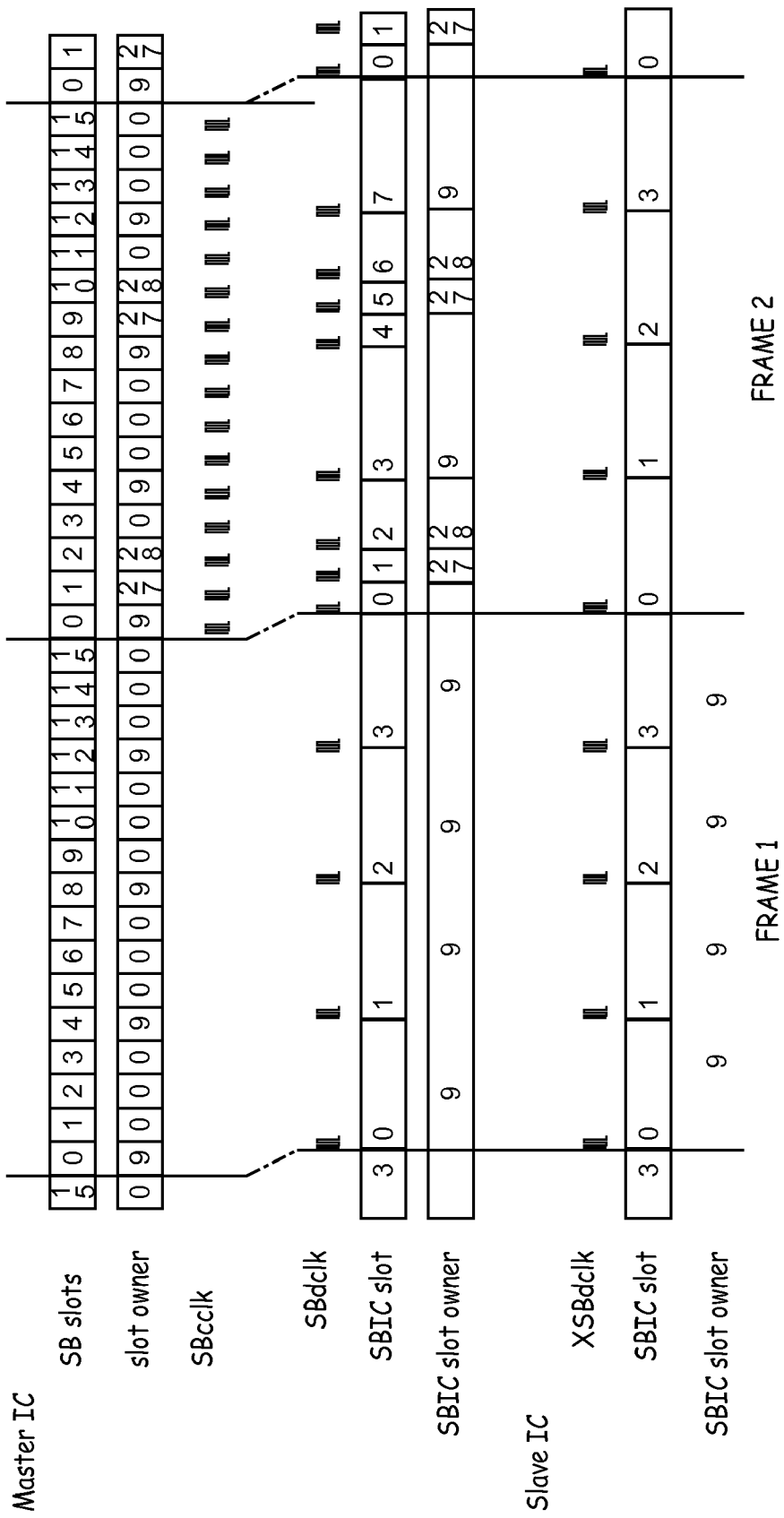

An example of reconfiguration of the streaming bus will now be discussed in greater detail. Turning now to FIG. 7, a timing diagram illustrates how the configuration clock SBCclk is used for reconfiguration. Specifically, FIG. 7 shows an example where the streaming bus includes 16 slots in each frame, and shows the current assignment of the 16 slots in the first frame, and the new assignment after configuration in the second frame. In the first frame, 4 slots have been previously assigned to the subsystem corresponding to slot owner 9. The streaming bus interface circuit corresponding to that subsystem would thus put data on the database on the transition of the data clock SBdclk in each of those four frames. Thus, slot owner 9 is able to transmit at four times the frame rate. The rest of the slots in the frame 1 are unassigned, as indicated by a 0 specified as the slot owner for those slots. It should be noted that the configuration clock SBcclk and the reconfiguration operation only operate when a change is required to configuration. Otherwise, the streaming bus controller only provides SBdclk and only SBdata is put on the bus.

In frame 2, the streaming bus controller initiates a reconfiguration of the streaming data bus by triggering the configuration clock SBCclk during each slot that is to be reconfigured. The configuration clock SBCclk clocks configuration data, and occurs in each slot before the data clock SBDclk that clocks bus data for that slot. In this example, the configuration clock SBCclk is triggered each slot, although that is not necessary if all slots are not to be reconfigured. On the transition of each SBCclk the corresponding slot is reassigned to a slot owner identified by data put on the bus by the bus controller. The streaming bus interface circuits read the data on the bus at each configuration clock SBCclk transition to determine who the slot is now assigned to. The new owner of the slot can then transmit in that slot. Thus, each slot in the reconfiguration frame operates according to the new configuration that is made within that slot.

In the first slot of the second frame, the slot owner is again assigned to slot owner 9. Thus, the slot owner 9 can continue to transmit data in that slot. In fact, the streaming bus interface circuit for slot owner 9 will immediately recognize that it still owns slot number 9, and will transmit data in the same slot on the transition of the data block SBdclk. Thus, the subsystem corresponding to slot owner 9 will continue to transmit in it assigned slots without any interruption, and thus without any jitter introduced into the flow of data from the subsystem.

On the second slot in the second frame, the slot owner is assigned to a new owner 27. Specifically, the streaming bus controller will assign the slot by putting a 27 on the data bus when the configuration clock SBcclk transitions in the second frame. From the configuration data but on the bus by the controller the streaming bus interface circuit corresponding to slot owner 27 will immediately recognize that it has been assigned this time slot, and can begin to put data in that slot on the transition of the data clock SBdclk. Thus, again, the slot is reassigned on the fly. This processes continues for each of the 16 slots in the second frame, with the third slot being assigned to the subsystem identified by slot owner 28, and the fifth slot being assigned to slot owner number 9, and so on. Slots in which a 0 was transmitted as slot owner are unassigned. When the second frame is completed, slot owner 9 will have been assigned to the four slots, the same for slots it was previously assigned to. Thus, transmissions from the subsystem corresponding to slot owner 9 will have continued through the reconfiguration process without interruption. Likewise, when the reconfiguration frame has been complete slot owners 27 and 28 will have each been assigned two slots in the frame, and have been able transmit data in their assigned slots. Thus, reconfiguration requires only 1 frame to complete, and does not require the interruption of any existing slot assignments or the transmission of data on those assigned slots.

It should be noted that typically the bus system would be configured initially, and would then only be reconfigured when operating parameters of the bus changed. Thus, the configuration clock SBcclk would only be provided in those relatively rare frames in which reconfiguration is to occur.

It should be noted that not all slots need to be routed to subsystems that are on external IC's. In the example of FIG. 7, data from some slots is routed both internally to the subsystems of the master IC and externally to the subsystems of the slave IC. Data in other slots is only routed to the subsystems of the master IC. Data that is routed only internally stays in the master IC. Specifically, the slave IC continues to see only four slots in the second frame, as the data from the owners 27 and 28 is not transmitted externally from the master IC to the slave IC. Thus, no external pins toggle and external bus interface circuits are "blind" to these slots.

To facilitate this separate bus data clocks are provided. Specifically, a separate external data clock (XSBdclk) signal is provided to the slave IC. The external data clock XSBdclk can be different then the internal SBdclk signal on the master. In the illustrated example, the SBdclk on the master IC has 8 cycles in the second frame to indicate 8 data transmissions, while the external data clock XSBdclk only has the 4 cycles that clock data that is routed to the external IC.

Likewise the data on the external bus itself, (XSBdata) can be different then the data on the master IC bus SBdata. However, reconfiguration data is preferably sent to all bus interface circuits, and thus the external configuration clock is the same as the SBcclk signal on the master IC.

Thus, the streaming bus system preferably provides the ability to reconfigure bus timing, routing or slot assignments without interrupting data periodicity or continuity. This allows subsystems to be added or subtracted, enabled or disabled without disrupting other data on the bus. Reconfiguration occurs at the beginning of a frame, allowing the previous frame to go to completion. Preferably, in addition to facilitating reassignment of slots, reconfiguration can include changing a variety of bus parameters, including slot length, frame rate, routing and bytes per slot. For reprogramming and reconfiguration, the streaming bus controller would typically be coupled to another bus, such as an event bus to receive instructions as any other subsystem would. Other than that, the streaming bus is generally run independently of other buses. The streaming bus is also suitably implemented for reset-independence such that subsystems can be reset independently without the risk of spreading resets to the entire system.

Reductions in power consumption are accomplished in several ways. For example, reductions in power consumption are achieved by gating certain clocks in the bus when no transmission is active, and minimizing the number of clocks per frame. Additionally, data not used outside the master IC is not transmitted other ICs. Finally, the bus is implemented to require only the transmission of data on the bus, without requiring the use of other bits for labels or headers. This again reduces the amount of power used by the bus.

As describe above, the streaming bus is implemented with streaming bus interface circuits for each subsystem that uses the streaming bus. The bus interface circuit provides the connection, buffering, timing and arbitration interface to the bus. The streaming bus also includes a streaming bus controller which controls a streaming bus configuration clock, a streaming bus data clock, and bus timing. The controller configures the bus to drive either only internally (on the master IC) or both externally and internally (to other ICs in addition to the master IC). Finally, the controller controls and determines the bus reconfiguration procedure.

Each streaming bus interface circuit takes data presented by the subsystem and sends it across the bus SBdata in sequential nibbles in its assigned slot. Likewise, all streaming bus interface circuits receiving data by latching sequential nibbles in SBdata and presenting them to their corresponding subsystem.

The bus interface circuits are implemented to put data on the bus only on the slots in which the corresponding subsystem is the owner, and when the data clock SBDclk is high.

Otherwise, the input to the bus is held at a high impedance. As one exemplary implementation, on the rising edge of the SBDclk the corresponding bus interface circuit drives the bus data SBdata. Then, on the falling edge of SBDclk all bus interface circuits release SBdata to high impedance, and capture SBdata to a destination register.

The streaming bus can use a variety of error control techniques, including bit parity checking and self-monitored test events, as well as procedures for subsystem power faults or internal sources of corruption.

A detailed example of a message bus will now be discussed. The message bus is implemented to deliver different types of larger messages to and from the subsystems in the implantable medical device. To best meet the different requirements of general message delivery, the message bus preferably includes the ability for data transfer synchronization of transmissions to multiple target subsystems. This provides the ability to ensure that messages need to be sent only once, thereby reducing the amount of power used to send messages to multiple target subsystems. In this technique, the message bus preferably sends a message header to all target subsystems and waits for acknowledgement from each target subsystem that they are ready to receive message data. When the message bus has received acknowledgement from each subsystem as to its readiness to receive the message, the message bus transmits the message to all of the subsystems at once. Thus, the message bus is able to reliably deliver the message while reducing the need for multiple transmissions that would otherwise waste significant power.

Like the streaming bus, the message bus system is preferably layered, with each higher layer using the functions of the lower layers but not specifying their implementation. As one example, the message bus can be conceptually layered into a system layer, application layer, session layer and a network layer. The system layer defines the overall functional objectives and partitions functions into different subsystems. The message bus is a functional complement to the event bus. The message bus has an unlimited frame length, is bidirectional, and allows for acknowledgements prior to sending.

Again, like the streaming bus, the message bus is implemented with message bus interface circuits for each subsystem that uses the message bus. The bus interface circuit provides the connection, buffering, timing and arbitration interface to the bus. The message bus also includes a message bus controller which controls a message bus clock, a message bus data clock, and frame stops and starts. The controller also configures the message bus to drive either only internally (on the master IC) or both externally and internally (to other ICs in addition to the master IC). The message bus also includes a message bus data driver for each IC. The driver buffers the external drive, controls data direction, and holds internal data while drivers are tristated.

In one embodiment, the message bus is comprised of 3 control signals, a clock signal MBclk, a request in signal MBreqin and a request out signal MBreqout, plus a 4-bit data bus MBdata. The message data transfer is synchronized by MBclk. Start/stop and some bus arbitration are controlled by MBreqin and MBreqout. Asynchronous system reset of the MBICs is provided by MBreset. MBdata, MBclk and MBreset connect in parallel to each subsystem as part of the bus (see bus 210 in FIG. 3). MBreqin/MBreqout connect between interface circuits in series (see the request lines 302 and 304 in FIG. 3).

Messages are bidirectional, unlike event data or streaming data. Data flow can be either from initiator to responder(s) in a write operation, or to initiator from a single responder in a read operation. Furthermore, each message frame includes a header, sent from the initiating subsystem to the target subsystems. Then, within that frame an acknowledgement (Ack) is received from the responding subsystems. The Ack is a feedback mechanism where any subsystem can communicate its readiness to respond to the message—whether it is its ability to consume incoming data (a write frame) or provide requested data (a read frame). When the required acknowledgements are received by the initiating subsystem, the body of the message is put on the bus. When the message is a write operation, the bytes making up the body of the message are put on the bus by the initiating subsystem. When the message is a read operation, the bytes making up the message are put on the bus by the responding subsystem. In either case, the message body can comprise a varying number of data bytes that are put on the data bus by the appropriate message bus interface circuit. Again, the message header, Ack, and message body are all considered part of the same message frame.

The header includes a message ID field that identifies the message. Sent at the beginning of the message frame, the header is received by each of the other bus interface circuits. The corresponding subsystems read the header and determine if the message is for them, and if they need to respond. Once a message header is transmitted across the bus, all subsystems evaluate it and determine in what mode they will participate in the message. Each subsystem can then send an acknowledgment back to the initiating subsystem.

The acknowledgement can take one of three forms. Specifically, each subsystem can choose "Ready" "Wait" or "Nack" (not ready), which is sent back to the initiating subsystem. Thus, any subsystems that need to respond will interpret the message ID, generate an appropriate Ack, and send the Ack back to the initiating subsystem through the bus interface circuits. For example, during a read the target subsystem will recognize the message and be the only subsystem to respond.

The initiating subsystems will wait until an Ack is received from each of the other required subsystems before sending the message body. Thus, the use of the Ack procedure allows responders to communicate readiness for data exchange. For example, if the responder needs time to prepare data (e.g. it is firmware-controlled), prepare space to receive data, or interrupt a CPU to handle data, it can request it through Ack. This reduces overall power consumption by assuring that the message body need only be sent once.

The message bus system is preferably implemented to provide arbitration. If multiple subsystems attempt bus access simultaneously, the message bus system must determine the order the subsystems get access to the message bus. This is generally referred to as arbitration. As discussed above, arbitration can be based on the physical origin of the message (subsystem priority) and on the context of the message (per-message priority). Per-message priority can be provided using priority lines activated by the bus interface circuits. In this case, bus access is regulated based on the message itself, independent of its physical origin. This can be used by system designers to give preferred bus access to some (priority) messages over other (nonpriority) messages. This ability serves to keep the base MBclk rate as low as possible, separating non-critical messages from peak traffic.

Some messages can be configured to be high-priority always, based on the importance of their information, or the criticality of their timing. Alternatively, messages could be assigned priority on-the-fly. For example, if a message sat in a bus interface circuit waiting to be transmitted, but the bus was being hogged by other users, a session layer could assign priority to the message to get it out. This helps to balance bus traffic and compensate against the rigid ordering imposed by the physically-ordered scheme.

Subsystem priority arbitrates by physical (hardwired) order of subsystems. Specifically, the order of subsystems as they are connected serially by the bus request lines, such as request lines 302 and 304 of FIG. 3. Thus, the earliest subsystems in the chain of bus interface circuits are given priority over later subsystems.

The request lines can also be used to arbitrate a message based on whether the message is coming from a bus interface circuit on an external IC or a bus interface circuit on the internal IC. Specifically, the chain of bus interface circuits on the internal IC can be coupled with the bus interface circuits on the external IC such that the external IC bus interface circuits are given precedence over the bus interface circuits on the internal IC. This can compensate for the lack of priority lines connected from the external IC to the bus controller.

A detailed example of an event bus will now be discussed. The event bus is configured to send event data between subsystems, where the event data are fixed length, relatively short data messages. The event data are used to reliably indicate that an important event has occurred, and to pass data associated with the event. For example, event data can be sent to notify other subsystems that a cardiac event has been detected, which will in turn cause other systems to activate and respond. Because the event data are relatively short and of defined length each entire event data packet can be fully buffered at the transmitter and receiver. This allows the transmitting subsystem to request an event data packet to be sent without requiring the transmitting subsystem to further monitor the bus. Furthermore, full buffering allows transmitting and receiving subsystems to run at different clocks or in different states of activation. Thus, one subsystem can communicate with another subsystem, even while the other subsystem is inactive. This ability to communicate with other subsystems that are inactive facilitates a high level of fault tolerance in the system. Furthermore, because the event data are relatively short it can be assured that an event data will be sent relatively quickly, without having to wait for a very long message to complete. This facilitates high reliability and high speed data transmission for the event bus messages. The event bus is also suitably implemented for reset-independence such that subsystems can be reset independently without the risk of spreading resets to the entire system.

Like the streaming bus, the event layer system is preferably layered, with each higher layer using the functions of the lower layers but not specifying their implementation. As one example, the event bus can be conceptually layered into a system layer, application layer, session layer and a network layer. The system layer defines the overall functional objectives and partitions functions into different subsystems.

Also, like the streaming bus, the event bus is implemented with event bus interface circuits for each subsystem that uses the event bus. The bus interface circuit provides the connection, buffering, timing and arbitration interface to the bus. The event bus also includes an event bus controller which controls an event bus clock, a event bus data clock, and frame stops and starts. The controller also configures the event bus to drive either only internally (on the master IC) or both externally and internally (to other ICs in addition to the master IC). The event bus also includes a message bus data driver for each IC. The driver buffers the external drive, controls data direction, and holds internal data while drivers are tristated.

The event bus gives a mechanism for subsystems to send short encoded events to each other. Each event is broadcast (i.e. there is no destination address) to all the other subsystems on the same IC, and to external IC's if requested by the bus interface circuit. The bus itself is half-duplex: only one event at a time can be on the bus. But, subsystems can simultaneously request event transmission while listening to incoming events from elsewhere.

A typical implantable medical device could include hundreds of signals that could be formatted and sent as event data on the event bus. As a result of partitioning, some of the events never are used outside their subsystem, so don't need broadcasting on the event bus. Some signal traffic between subsystems won't make good events, and may use dedicated pins or wires for functional or timing reasons or to save power or bus bandwidth. It is expected there will be a few hundred different events that use the event bus, and that most or all subsystems will be served by this bus.

To simplify arbitration and buffering the size of event data is limited. In one embodiment, each event data is formatted into a header and data portions. For example, event data can be limited to be between 1 and 4 bytes long, with the first byte comprising an event ID. The event bus would typically be used to indicate a change of state. For example, in a typical implantable medical device a signal will go high go high to indicate "telemetry on," and some time later go low to indicate "telemetry off." Each of these change of states could be described by an event data on.

It should be noted that a long series of data bytes can be sent across the event bus, using multiple event data. To the data link layer the transfer appears to be many events. But applications and sessions may consider the long sequence to be a "virtual message." Because a series of event data could delay more critical events, it is generally desirable to deprioritize any virtual message. Furthermore, the transit time of the virtual message could be quite long, interleaved with normal events. The session layers of the participating subsystems would need to recognize and reassemble the virtual message.

Several subsystems may request a transmission at about the same time, so that the data link layer must resolve which EBIC can transmit. Arbitration of bus access is not done in one central location, but is done by the event bus interface circuits and event bus controller working in concert.

In one embodiment the event bus is comprised of 4 control signals and a four bit wide data bus EBdata. The control signals are the event bus clock EBclk, request lines EBreqin and EBreqout and a reset line EBreset. The event data transfer is synchronized by the event bus clock EBclk. Start and stop, and bus arbitration are controlled by the request lines EBreqin and EBreqout. The reset signal EBreset provides asynchronous system reset of the bus interface circuits. EBdata, EBclk and EBreset connect in parallel to each subsystem (see bus 210 in FIG. 3). EBreqin/EBreqout connect between interface circuits in series (see the request lines 302 and 304 in FIG. 3).

An event frame is the timespan in which one event is arbitrated, sent, and the event bus interface circuits reset for the next frame. The event bus is re-arbitrated for new ownership each frame. A frame once initiated goes to completion—there is no preemption, restart or recall. All event bus interface circuits will share the same frame timing, although the EBclk to each may be skewed. The number of bytes of data transferred during the event frame is allowed to vary from 1 to 4. So each subsystem must be able to recognize the start and stop time. This information is provided through EBreq and EBclk. Event start is indicated by the first negative edge of EBclk after a stop event. Event stop is indicated by the first negative edge of EBclk with EBreqin low.

Transmitting is done individually, but all event bus interface circuits receive if they are provided EBclk. Event bytes are broadcast serially on EBdata, always updated on the positive edge of EBclk. Because of clock skew, it is preferable that EBdata be viewed or loaded by the bus interface circuits on the negative edge of EBclk.

As discussed above with reference to the streaming bus, the event bus also preferably includes an event reference clock (ESclk) which is routed to the subsystem. This clock is preferably synchronized to other clocks and behaviors throughout the system, and is preferably coordinated with EBclk frequency. Specifically, the event reference clock is used to sync the streaming bus to the event bus. Syncing the streaming bus with the reference clock means that streaming bus frames are synced with the event clock, thus facilitating communication between the systems.

Like the message bus, the event bus system is preferably implemented to provide arbitration. If multiple subsystems attempt bus access simultaneously, the event bus system must determine the order the subsystems get access to the event bus. Like the message bus, arbitration can be based on the physical origin of the message (subsystem priority) and on the context of the event (per-event priority). Per-message priority can be provided by priority lines activated by the bus interface circuits. In this case, bus access is regulated based on the event itself, independent of its physical origin. This can be used by system designers to give preferred bus access to some (priority) events over other (nonpriority) events. This ability serves to keep the base EBclk rate as low as possible, separating noncritical events from peak traffic.

Subsystem priority arbitrates by physical (hardwired) order of subsystems. Specifically, the order of subsystems as they are connected serially by the bus request lines, such as request lines 302 and 304 of FIG. 3. Thus, the earliest subsystems in the chain of bus interface circuits are given priority over later subsystems.

The present invention thus provides a bus system and method for implantable medical devices. The bus system provides for flexible and reliable communication between subsystems in an implantable medical device, such as an implantable cardiac defibrillators, implantable pulse generators, and implantable cardiac monitors. The bus system can be used to facilitate a wide variety of communications between various subsystems. These various subsystems can include one or more sensing devices (e.g., magnetic sensor, pressure sensor, motion sensor, ECG sensor), processors, data storage devices, patient alert devices, power management devices, signal processing and other devices implemented to perform a variety of different functions.

The bus system further provides for the rapid development cycle for implantable medical devices by facilitating subsystem modularity. Specifically, the bus system can be implemented to decouple the subsystems, allowing the subsystems to be removed, added or modified with limited amounts of customization required. Furthermore it can be implemented to facilitate the adding a new features without requiring a change the implementation of other features. This reduces the amount of required redesign and can also reduce the requirements for regulatory approval of the additional features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. An implantable medical device bus system, comprising:
   a streaming bus delivering periodic data between a plurality of subsystems of an implantable medical device, the streaming bus includes a plurality of streaming data conductors, a data clock conductor, and a configuration clock conductor;
   a plurality of bus interface circuits coupled to the streaming bus, each of the plurality of bus interface circuits coupled to one of the plurality of subsystems in the implantable medical device;
   a streaming bus controller coupled to the streaming bus, the streaming bus controller multiplexes the streaming bus into a plurality of time slots per frame for transmitting streaming data on the streaming data conductors, the streaming bus controller selectively sending configuration clock signals on the configuration clock conductor with configuration data on the streaming data conductors between the streaming data on the streaming data conductors within a single frame, the configuration data assigning time slots in the plurality of time slots to one or more of the subsystems in the implantable medical device, wherein a streaming data byte is broadcast on the streaming bus in an assigned time slot with no destination address.

2. The implantable medical device bus system of claim 1 wherein the configuration data assigns time slots in the plurality of time slots without disrupting the streaming data on the streaming data conductors being transmitted within the single frame during time slots previously assigned during a previous frame.

3. The implantable medical device bus system of claim 1 wherein the streaming bus controller sends a streaming bus data clock signal in each time slot to indicate the streaming data.

4. The implantable medical device bus system of claim 1 wherein the streaming data comprises sensor data from a sensor on the implantable medical device.

5. The implantable medical device bus system of claim 1 wherein the streaming bus controller selectively sends an external streaming bus data clock to bus interface circuits in the plurality of bus interface circuits on an external integrated circuit, the external streaming bus data clock signaling only time slots assigned on the external integrated circuit.

6. The implantable medical device bus system of claim 1 wherein the implantable medical device comprises an implantable cardiac device, and wherein the streaming data comprises sensor data selected from the group of electrical data, ECG data, accelerometer data and pressure data.

7. The implantable medical device bus system of claim 1 wherein the bus interface circuits receive and recognize streaming data on the streaming data conductors based on time slot location in the plurality of time slots per frame.

8. The implantable medical device bus system of claim 1 wherein each of the plurality of bus interface circuits can be selectively assigned more than one time slot per frame to provide an increased data transmission rate.

9. The implantable medical device bus system of claim 1 wherein each of the plurality of bus interface circuits can be selectively configured to skip frames to provide a reduced data transmission rate.

10. The implantable medical device bus system of claim 1 wherein the streaming bus provides a precise bus latency by assigning a repeating at least one time slot in the plurality of timeslot to a subsystem in the implantable medical device.

11. An implantable medical device bus system, comprising:
- a message bus delivering large messages between a plurality of subsystems included in an implantable medical device, the message bus including a plurality of bidirectional message data conductors and a message data clock conductor;
- a plurality of bus interface circuits coupled to the message bus, each of the plurality of bus interface circuits coupled to one of the plurality of subsystems in the implantable medical device;
- request line conductors, the request line conductors coupling the bus interface circuits into a series;
- a message bus controller coupled to the message bus and the request line conductors, the message bus system arbitrating messages on the message bus according to order of the series of transmitting bus interface circuits, wherein an initiating one of the plurality of bus interface circuits sends a message header on the request line conductors to each of the other of the plurality of bus interface circuits, each of the other of the plurality of subsystems reads the header and determines if a response is required, and a responding one of the plurality of bus interface circuits sends a synchronized transmission of a message body on the plurality of bidirectional message data conductors in response to the message header.

12. The implantable medical device bus system of claim 11 wherein the responding one of the plurality of bus interface circuits waits until an acknowledgement is received from at least one other of the plurality of bus interface circuits in response to the message header before sending the message body.

13. The implantable medical device bus system of claim 12 wherein the initiating one of the plurality of bus interface circuits is the same as the responding one of the plurality of bus interface circuits in a write operation.

14. The implantable medical device bus system of claim 12 wherein the initiating one of the plurality of bus interface circuits is different from the responding one of the plurality of bus interface circuits in a read operation.

15. The implantable medical device bus system of claim 12 wherein the responding bus interface circuit delays the synchronized transmission of the message body in response to a wait acknowledgement received from one of the plurality of bus interface circuits.

16. The implantable medical device bus system of claim 11 wherein the bus system further includes priority line conductors, the priority line conductors coupling to the bus interface circuits, and wherein the bus interface circuits can request precedence for transmitting on the priority line conductors.

17. The implantable medical device bus system of claim 16 wherein priority line conductors includes an external priority line for requesting precedence for transmitting to subsystems on an external integrated circuit and an internal priority line for requesting precedence for transmitting only to subsystems within an integrated circuit.

18. An implantable medical device bus system, comprising:
- a streaming bus delivering periodic data between a plurality of subsystems of an implantable medical device, the streaming bus including a plurality of streaming data conductors;
- a plurality of streaming bus interface circuits coupled to the streaming bus, each of the plurality of streaming bus interface circuits coupled to one of the plurality of subsystems in an implantable medical device, the streaming bus interface circuits transmitting streaming data on the streaming bus in a plurality of assigned time slots, wherein a streaming data byte is broadcast on the streaming bus in an assigned time slot with no destination address;
- a message bus delivering large messages between the plurality of subsystems, the message bus including a plurality of message data conductors;
- a plurality of message bus interface circuits coupled to the message bus, each of the plurality of message bus interface circuits coupled to one of the plurality of subsystems in the implantable medical device, the message bus interface circuits sending message data on the message bus;
- an event bus sending event data between the plurality of subsystems, the event bus including a plurality of event data conductors; and
- a plurality of event bus interface circuits coupled to the event bus, each of the plurality of event bus interface circuits coupled to one of the plurality of subsystems in the implantable medical device, the event bus interface circuits sending event data on the event bus, the event data having a limited data length, wherein each of the streaming data bus, the message bus and the event bus being coupled to each of the plurality of subsystems in the implantable medical device via the respective streaming bus interface circuits, the message bus interface circuits and the event bus interface circuits.

19. The implantable medical device bus system of claim 18 further comprising a streaming bus controller coupled to the streaming bus, the streaming bus controller multiplexing the streaming bus into a plurality of time slots per frame for transmitting streaming data on the streaming data conductors, the streaming bus controller selectively sending configuration clock signals on a configuration clock conductor with configuration data on streaming data conductors between the streaming data on the streaming data conductors within a single frame, the configuration data assigning time slots in the plurality of time slots to one or more of the subsystems in the implantable medical device.

20. The implantable medical device bus system of claim 18 further comprising a message bus request line conductors, the message bus request line conductors coupling the message bus interface circuits into a series, and further comprising a message bus controller coupled to the message bus and the request line controllers, the message bus system arbitrating messages on the message bus according to order of the series of transmitting message bus interface circuits.

21. The implantable medical device bus system of claim 18 further comprising an event bus request line conductors, the event bus request line conductors coupling the event bus interface circuits into a series, and further comprising a event bus controller coupled to the event bus and the request line controllers, the event bus system arbitrating messages on the message bus by according to order of the series of transmitting event bus interface circuits.

22. The implantable medical device bus system of claim 18 wherein the plurality of assigned time slots in the streaming bus repeat by a frame, and wherein the frame coincides with an event bus clock.

23. The implantable medical device bus system of claim 18 wherein the plurality of event bus interface circuits each include a data buffer, the data buffer large enough to store an entire event data.

24. The implantable medical device bus system of claim 18 wherein a time slot begins operating within the single frame according to a new time slot assignment made within the time slot.

25. The implantable medical device bus system of claim 18 wherein an event is broadcast on the event bus by a broadcasting one of the plurality of subsystems to all the other plurality of subsystems.

26. The implantable medical bus system of claim 25 wherein an initiating one of the plurality of subsystems sends a message header on the request line conductors to each of the other of the plurality of subsystems and each of the other of the plurality of subsystems reads the header and determines if a response is required.

27. An implantable medical device bus system, comprising:
- a streaming bus delivering periodic data between a plurality of subsystems of an implantable medical device, the streaming bus including a plurality of streaming data conductors;
- a plurality of streaming bus interface circuits coupled to the streaming bus, each of the plurality of bus interface circuits coupled to one of a plurality of subsystems in an implantable medical device;
- a streaming bus controller coupled to the streaming bus and including a streaming bus clock, the streaming bus controller multiplexes the streaming bus into a plurality of time slots per frame for transmitting streaming data on the streaming data conductors, the streaming bus controller selectively sending configuration clock signals on the configuration clock conductor with configuration data on the streaming data conductors between the streaming data on the streaming data conductors within a single frame, the configuration data assigning time slots in the plurality of time slots to one or more of the subsystems in the implantable medical device wherein an assigned time slot begins operating within the single frame according to a new time slot assignment made within the assigned time slot, wherein a streaming data byte is broadcast on the streaming bus in an assigned time slot with no destination address;
- a message bus delivering large messages between a plurality of subsystems included in an implantable medical device, the message bus including a plurality of message data conductors;
- a plurality of message bus interface circuits coupled to the message bus, each of the plurality of message bus interface circuits coupled to one of the plurality of subsystems in the implantable medical device, the message bus interface circuits sending message data on the message bus;
- an event bus sending event data between the plurality of subsystems, the event bus including a plurality of event data conductors, an event bus clock and an event reference clock coordinated with the event bus clock; and
- a plurality of event bus interface circuits coupled to the event bus, each of the plurality of event bus interface circuits coupled to one of the plurality of subsystems in the implantable medical device, the event bus interface circuits sending event data on the event bus, the event data having a limited data length,
- the event reference clock synchronized with the streaming bus clock to synchronize streaming bus frames with the event reference clock,
- each of the streaming bus, the message bus and the event bus coupled to each of the plurality of subsystems in the implantable medical device via the respective streaming bus interface circuits, message bus interface circuits, and event bus interface circuits.

* * * * *